(12) United States Patent
Uibel et al.

(10) Patent No.: US 7,973,926 B1
(45) Date of Patent: Jul. 5, 2011

(54) METHODS FOR DETERMINING OLEFIN CONCENTRATIONS IN OLEFIN-CONTAINING FUELS

(75) Inventors: Rory H. Uibel, Salt Lake City, UT (US); Robert E. Benner, Salt Lake City, UT (US); Eric R. Jacobsen, Salt Lake City, UT (US); Lee M. Smith, Salt Lake City, UT (US)

(73) Assignee: Process Instruments, Inc., Salt Lake City, UT (US)

( * ) Notice: Subject to any disclaimer, the term of this patent is extended or adjusted under 35 U.S.C. 154(b) by 386 days.

(21) Appl. No.: 12/355,040

(22) Filed: Jan. 16, 2009

(51) Int. Cl.
*G01J 3/44* (2006.01)

(52) U.S. Cl. ...................................................... 356/301

(58) Field of Classification Search .................... 356/301
See application file for complete search history.

(56) References Cited

U.S. PATENT DOCUMENTS

| | | | | |
|---|---|---|---|---|
| 5,046,854 A | * | 9/1991 | Weller et al. | 356/440 |
| 5,684,580 A | * | 11/1997 | Cooper et al. | 356/301 |
| 5,751,415 A | * | 5/1998 | Smith et al. | 356/301 |
| 6,100,975 A | * | 8/2000 | Smith et al. | 356/301 |

\* cited by examiner

*Primary Examiner* — Kara E Geisel
(74) *Attorney, Agent, or Firm* — Kirton & McConkie; Evan R. Witt

(57) ABSTRACT

Systems and methods for determining olefin concentrations in olefin-containing fuels (e.g., gasoline) are described. Generally, a Raman spectrum from a linear-calibration reference sample (e.g., a pure hydrocarbon, such as toluene) and Raman spectra from multiple simulated fuel samples having known olefin concentrations are obtained. An area ratio for each simulated fuel sample is created by dividing the area in the olefin region of each fuel sample by the area in the chemical spectral region of the linear-calibration reference sample. The area ratio and the known olefin concentration for each simulated sample are used to create a linear olefin calibration. The olefin concentration of a fuel sample with an unknown olefin concentration is calculated by determining the area ratio between the olefin spectral region in the unknown sample and the chemical spectral region in a concentration-calculation reference sample (e.g., toluene) and placing the new area ratio into the linear olefin calibration.

20 Claims, 9 Drawing Sheets

METHODS FOR DETERMINING OLEFIN CONCENTRATIONS IN OLEFIN-CONTAINING FUELS

BACKGROUND OF THE INVENTION

1. Field of the Invention

This disclosure relates to systems and methods for determining olefin concentrations in an olefin-containing fuel. More particularly, this disclosure discusses methods for determining olefin concentrations in gasoline mixtures through the use of Raman spectroscopy and a pure reference sample.

2. Background and Related Art

The refining and processing of crude petroleum into commercially useful petroleum products is a vital industry around the world. One of the most important petroleum products is the class of gasoline fuels. Generally, gasoline fuels comprise a mixture of various hydrocarbon compounds, which typically have between 4 and 12 carbon atoms per molecule. Some examples of such hydrocarbons can include n-paraffins, naphthenes, olefins, and a variety of aromatic compounds, such as toluene and benzene. The concentration and chemical grouping of the various hydrocarbons determines the resulting properties of the gasoline fuel, such as the fuel's octane rating.

The octane rating for a gasoline fuel is defined in terms of its pre-detonation, or knocking, characteristics relative to a standard blend of isooctane (2,3,4-trimethylpentane) and n-heptane. Arbitrarily, an octane number of zero has been assigned to n-heptane and a rating of 100 to isooctane. Thus, an unknown fuel having a knocking tendency equal to a blend of 90% isooctane and 10% n-heptane, by volume, is assigned an octane number of 90.

Because a gasoline fuel with a higher octane rating may be sold at an increased price, many gasoline fuel producers seek to increase gasoline octane ratings in a manner that does not significantly increase the production costs of the fuel. Gasoline producers may increase a gasoline fuel's octane rating in a variety of manners. For example, a producer may enhance a fuel's octane rating by adding isooctane, aromatics, and/or olefins to the fuel. However, because isooctane and aromatics tend to be more expensive than olefins, many gasoline producers prefer to increase a fuel's octane rating through the addition of olefins.

Nevertheless, because olefins may be photo-reactive and form smog when burned in internal combustion engines, many governments across the world limit olefin levels in gasoline. In many cases, these olefin regulations continue to become more stringent. Accordingly, to ensure high octane levels and compliance with government environmental regulations, many gasoline producers seek to measure the olefin levels in the gasoline fuels they produce.

Currently, olefin levels in gasoline are measured and predicted in a variety of ways, including through the use of supercritical fluid chromatography ("SFC", ASTM-D6550-05), fluorescent indicator absorption ("FIA", ASTM-D1319), and chemometric modeling. However, such techniques may have significant shortcomings. By way of example, SFC may require the use of expensive equipment and chemicals at high pressures, which make the chemicals hard to handle. For instance, SFC may require the use of high purity carbon dioxide (e.g., 99.99% pure), high purity nitrogen (e.g., 99.99% pure), and/or hydrocarbon-free air (e.g., a very clean compressed air) at pressures that are greater than 3,000 psi. Additionally, certain SFC techniques are inaccurate at determining the olefin concentrations from multiple gasoline samples, especially where the olefin levels are relatively high. Because such SFC techniques may have a relatively high standard error, in order to comply with government regulations, many gasoline producers must limit the olefin content in their gasoline to an amount within the error of the detection technique. Such gasoline producers could include more olefins in gasoline if the producers were able to more accurately measure the olefin levels.

In another example, FIA may have several shortcomings. For instance, FIA can be a relatively time consuming process. Indeed, in some cases, an FIA testing procedure may take from about 2 to about 3 hours from start to finish. Additionally, FIA may not be suitable for use with fuels that contain alcohol, such as methanol, ethanol, butanol, and other oxygenates such as tertiary-amyl methyl ether (TAME) and methyl tertiary butyl ether (MTBE), and so forth. The disadvantages associated with this inability to properly test alcohol-containing fuels can become even more pronounced as fuel producers try to conserve oil by blending fuels with alcohol. Furthermore, FIA testing procedures may often be inaccurate from one test to another or from user to another. For instance, FIA requires a user to pack a column with a silica gel that is used to separate the various components of the fuel (e.g., paraffins, aromatics, olefins, etc.). However, because one user may pack one column differently than another column, or because one user may pack a column differently than another user, the FIA results from one column may vary from the results of another column.

In some cases, a gasoline that contains lower olefin levels may have a lower octane rating than is desired. Accordingly, such gasoline may sell for a lower price. In other cases, in order to maintain a high octane rating, a gasoline producer may have to add components (e.g., isooctane, aromatics, and the like) that are more expensive than olefins. In sum, the measurement errors associated with standard SFC and FIA have caused many gasoline producers to have lower profit margins than would have been possible if the producers had been able to more accurately measure the olefin levels in gasoline.

Although chemometric modeling may work well at accurately determining key gasoline parameters (e.g., olefin levels) for on-line and laboratory analysis of routine samples, chemometric modeling may not accurately determine gasoline properties for new types of gasoline blends or gasoline samples from different refineries that contain unique spectral features, which were not previously included in the model. Indeed, where the gasoline blend comprises a new spectral feature, the chemometric model may need to be updated in order to accurately predict desired parameters.

Thus, while techniques currently exist that are used to determine olefin levels in gasoline fuels, challenges still exist, including those listed above. Accordingly, it would be an improvement in the art to augment or even replace current techniques with other techniques.

BRIEF SUMMARY OF THE INVENTION

This disclosure discusses systems and methods for using Raman spectroscopy to determine the olefin concentration of an olefin-containing fuel. While the described methods may be used to determine the olefin concentration of virtually any suitable olefin-containing fuel, such as a gasoline, a gasoline biofuel, a diesel fuel, diesel biofuel, and/or a jet fuel, in some preferred implementations, the methods described herein are used to determine olefin levels in gasoline. Additionally, while the methods may use virtually any type of Raman spectroscopy that is capable of determining olefin levels in an olefin-containing fuel, in some presently preferred implementations, the described methods implement near-infrared Raman spectroscopy.

Often, the wavelength of a laser in a Raman spectrometer varies as the laser ages. To overcome laser wavelength variations, the described methods may include methods to automatically update or compensate for slight variations in the laser's wavelength. This automatic updating may occur in any suitable manner. In one example, the wavelength updating method involves obtaining a known Raman spectrum from a pure reference sample (e.g., a sample of a pure hydrocarbon, such as toluene). For simplicity, this reference sample is referred to as a first laser-calibration reference sample. After determining the laser excitation wavelength that was used to obtain the known Raman spectrum and after determining the peak frequency shift of the first pure laser-calibration reference sample in the known Raman spectrum, a second laser-calibration reference sample containing the same chemical composition as the first laser-calibration reference sample is run through the Raman spectrometer. By comparing the peak frequency shift of the chemical in the known Raman spectrum with the peak frequency shift of the chemical in the Raman spectrum from the second laser-calibration reference sample, the actual laser excitation wavelength that was used to produce the Raman spectrum for the second laser-calibration reference sample may be calculated. With this information, the laser wavelength may automatically be determined and be used to calculate the frequency shift of other Raman spectra, such as olefin Raman peaks, which generally occur in a spectral region between about 1635 and about 1725 $cm^{-1}$.

In accordance with the described methods, a Raman spectrometer may be used in any suitable manner to determine olefin levels in an olefin-containing fuel. In one non-limiting example, the method includes a technique that accounts for slight variations in the Raman spectrometer throughput. For example, spectrometer instrument throughput differences may be caused by variances in fiber-optic coupling, laser power, filter efficiency, debris on the sample cell window, optical lens clouding, etc. One non-limiting technique involves fitting a linear calibration curve to a plot of calibration area ratios vs. known olefin concentrations for a plurality of simulated fuel samples and then using the linear calibration to determine the olefin concentration in an actual fuel sample.

The linear calibration curve may be created by any suitable method. In one example of a suitable method, a Raman spectrometer is used to obtain a Raman spectrum from a pure reference sample (e.g., toluene), which, for simplicity, is referred to as a linear-calibration reference sample. In this example, Raman spectra are also collected from multiple simulated fuel samples having known olefin concentrations. Further, in this example, a calibration area ratio for each simulated fuel sample is created by dividing the area in the olefin spectral region of the simulated fuel sample (e.g., between about 1635 and about 1725 $cm^{-1}$) by the area in the chemical spectral region of the linear-calibration reference sample. The calibration area ratio and the known olefin concentration for each simulated fuel sample may be plotted. A linear calibration described by the equation (Olefin vol %=(M·(area ratio)+B)) may then be fit to the plot. In the equation, M describes the slope and B describes the Y-intercept of the linear calibration curve.

With the linear calibration curve, the olefin concentration of an actual fuel sample comprising an unknown olefin concentration may be determined in any suitable manner. In one example, a Raman spectrum for a fuel sample with an unknown olefin concentration is obtained. To determine the olefin concentration of the unknown sample, by volume percent, a test area ratio is created by dividing the area in the olefin spectral region (e.g., 1635 to 1725 $cm^{-1}$) from the unknown sample by the area of the chemical spectral region from a pure reference sample (e.g., a sample of the same chemical in the linear-calibration reference sample), referred to as concentration-calculation reference sample. This test area ratio may then be used as the area ratio variable in the equation describing the linear calibration. With the slope and the intercept of the linear calibration curve and the test area ratio for the unknown sample, the concentration of the olefin in the unknown sample may be solved algebraically.

These features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which.

DETAILED DESCRIPTION OF THE INVENTION

Figure 1:
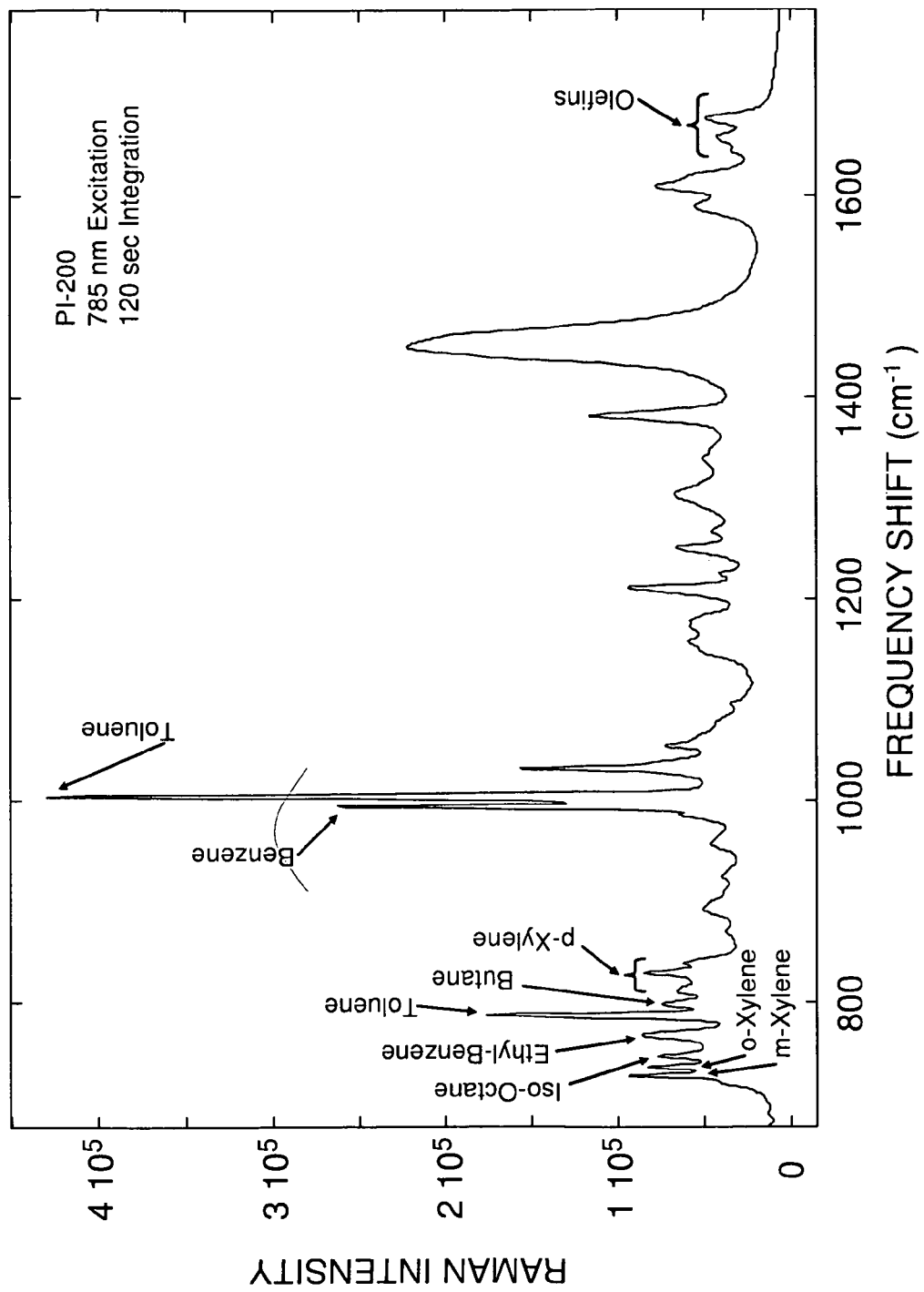
FIG. 1 illustrates a representative embodiment of a Raman spectrum from a gasoline stream.

Reference throughout this specification to "one embodiment," "a representative embodiment," or similar language, means that a particular feature, structure, or characteristic described in connection with the embodiment is included in at least one embodiment of the present invention. Thus, appearances of the phrases "in one embodiment," "in a representative embodiment," and similar language throughout this specification may, but do not necessarily, all refer to the same embodiment.

Furthermore, the described methods, elements, or characteristics of the invention may be combined in any suitable manner and in one or more embodiments. In the following description, numerous specific details are provided, such as examples of suitable Raman spectrometers, materials, chemicals, apparatus, processes, methods, etc., to provide a thorough understanding of embodiments of the invention. One skilled in the relevant art will recognize, however, that the invention may be practiced without one or more of the specific details or methods, or with other methods, components, characteristics, materials, and so forth. In other instances, well-known structures, materials, methods, or techniques are not shown or described in detail to avoid obscuring aspects of the invention.

The embodiments within the scope of the present invention will be best understood by reference to the Figures, wherein like parts are designated by like numerals throughout. It will be readily understood that the elements of the present invention, as generally described and illustrated in the Figures herein, could be arranged and designed in a wide variety of different configurations. Thus, the following more detailed description of the embodiments of the systems and methods for determining olefin concentrations in olefin-containing fuels, as represented in FIGS. 1 through 8, is not intended to limit the scope of the invention, as claimed, but is merely representative of the embodiments of the invention.

This disclosure discusses methods for using Raman spectroscopy to determine the olefin concentration of an olefin-containing fuel. As used herein, the terms olefin and olefins may refer to any alkene, or unsaturated hydrocarbon containing at least one carbon to carbon double bond ("C═C bond"), which is suitable for inclusion in a fuel. Additionally, as used herein, the term olefin-containing fuel may refer to any fuel source that contains an olefin and which is suitable for spectroscopic analysis with a Raman spectrometer. Some examples of olefin-containing fuels may include any suitable type of gasoline (e.g., regular unleaded, mid-grade, premium, etc.), gasoline bio-fuels (e.g., E85, and other alcohol-containing fuels), diesel (e.g., petro-diesel, ultra-low sulfur diesel, synthetic diesel, biodiesel, biomass to liquid diesel, gas to liquid diesel, etc.), and jet fuel. In some presently preferred embodiments, however, the described methods are used to determine olefin concentrations in gasoline. To provide a better understanding of the described methods, the following description discusses Raman spectroscopy followed by examples of methods for using Raman spectroscopy to determine olefin concentrations in an olefin-containing fuel (e.g., gasoline).

Generally, Raman spectroscopy relies on inelastic scattering, or Raman scattering, of monochromatic light that is produced by a laser in the visible, near infrared, or near ultraviolet range. The laser light may interact with phonons or other excitations in the sample that is being tested ("test sample") and result in the energy of the laser photons being shifted up or down. By measuring the molecular vibrational frequencies of the chemicals within the test sample, Raman spectroscopy may determine, or allow for the determination of, the chemical makeup of the test sample. Additionally, by measuring the strength of the optical interactions of the chemicals within the test sample, Raman spectroscopy may determine, or allow for the determination of, the molecular concentrations of the chemicals within the test sample.

The Raman spectrometer may display the spectroscopic results of the test sample as a Raman spectrum. Typically, a Raman spectrum comprises of a graph in which the peak frequency shift, or the location of one or more peaks on the X-axis, indicates the identity of a chemical in the test sample. Similarly, in a Raman spectrum, the area under the peak(s) of an individual chemical, or the area in a spectral region of a particular chemical, may directly correlate to the concentration of that particular chemical. For example, where the test sample has twice as much of a first chemical as it does a second chemical, the spectral region of the first chemical may be twice as large as the spectral region of the second chemical, assuming their Raman cross sections are equal.

FIG. 1 shows a representation of a typical Raman spectrum of a gasoline sample. As described above, the location of the peaks along the X-axis indicates the types of chemicals present in the gasoline (e.g., m-xylene, o-xylene, isooctane, ethyl-benzene, toluene, butane, p-xylene, benzene, olefins, etc.) and the area under the peaks, or the spectral regions, represents the amount of the individual chemicals present in the test sample. For instance, FIG. 1 indicates the presence of olefins between about 1635 and about 1725 $cm^{-1}$. Similarly, FIG. 1 illustrates that olefin molecules tend to have a distinct frequency shift that is not populated by other chemicals found in gasoline.

The Raman scattering cross sections (relative signal intensity) was measured for representative olefins, comprised of samples with C5, C6, C7, and C8 carbon numbers. Olefins of these carbon numbers comprise the majority of the many different olefin species observed in gasoline. It was found that the Raman scattering cross sections are about the same for these different types of olefins. Any differences in Raman scattering cross sections from the many different olefins in gasoline should even be smaller as an average of all the many different olefins that can occur in gasoline. This allows one to apply an area calibration curve derived from representative, laboratory-prepared, gravimetrically measured olefin samples to the prediction of real-world, gasoline samples containing many different olefin types.

Figure 2:
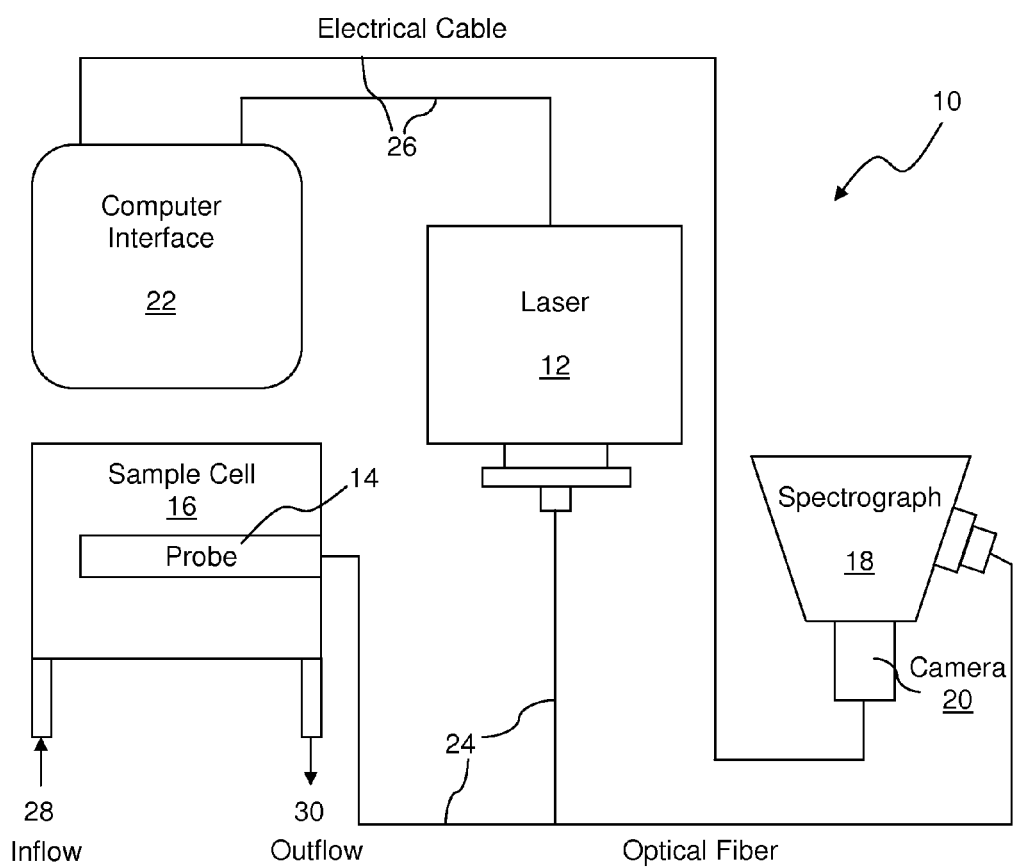
FIG. 2 illustrates a block diagram of a representative embodiment of a Raman spectrometer.

The described methods may incorporate any type of Raman spectroscopy that is capable of producing a Raman spectrum that includes the peak frequency shift and spectral region for one or more components of an olefin-containing fuel, such as gasoline. Some examples of suitable types of Raman spectroscopy may include near-infrared Raman spectroscopy, surface enhanced Raman spectroscopy ("SERS"), hyper Raman spectroscopy ("HRS"), resonance Raman spectroscopy ("RRS"), spontaneous Raman spectroscopy, stimulated Raman spectroscopy, Raman optical activity spectroscopy, coherent anti-stokes Raman spectroscopy, and/or spatially offset Raman spectroscopy. In addition to, or in place of, Raman spectroscopy, the described techniques may be performed with any other suitable spectroscopic technique, such as near-infrared absorption. In some presently preferred embodiments, however, the described methods implement near-infrared Raman spectroscopy.

Where the described methods implement near-infrared Raman spectroscopy, the Raman spectrometer may comprise any suitable component that allows the spectrometer to be sufficiently sensitive to accurately detect olefin signals in an olefin-containing fuel (e.g., gasoline). By way of non-limiting illustration, FIG. 2 depicts a block diagram of representative embodiment of a suitable near-infrared Raman spectrometer 10. Specifically, FIG. 2 shows that the Raman spectrometer 10 comprises a frequency-stabilized laser 12 (e.g., a long-life diode laser) for optical excitation, a fiber-optic probe 14 with optical filtering for guiding the excitation light to a sample cell 16 and directing the Raman scattered light to a spectrograph 18 (e.g., a compact optically-robust spectrograph), a charge-coupled device ("CCD") camera 20 (e.g., a 4-stage TE-cooled CCD camera with high quantum efficiency for full-spectrum detection), and a computer interface 22. Furthermore, FIG. 2 shows that the various components may be connected to each other in any suitable manner, including through the use of optical fibers 24 and/or electrical cables 26. One example of a suitable near-infrared Raman spectrometer is the PROCESS INSTRUMENTS® PI-200-L Raman Instrument.

In addition to the aforementioned components, a near-infrared Raman spectrometer may comprise any other suitable component or characteristic that allows it to accurately detect olefin in an olefin-containing fuel. In one example, FIG. 2 shows the sample cell 16 comprises a flow through cell that incorporates the fiber-optic probe 14. In this example, the sample cell 16 is designed to ensure that no laser radiation is visible to the operator. The flow through cell has minimal dead space and can be easily cleaned if necessary. Additionally, in this example, the fiber-optic probe may be protected from the sample stream by a sapphire flow cell window (not shown).

In another non-limiting example, a Raman spectrometer comprises an automatic sampling unit that automatically flushes different test samples through the sample cell. While the automatic sampling unit may function in any suitable manner, in some embodiments, the automatic sampler employs a positive pressure that pushes the test sample through the sample cell. By way of illustration, FIG. 2 shows that the test sample may flow through the inflow 28, past the probe 14, and out the outflow 30. In some embodiments, the automatic sampler further employs a continuous positive pressure to ensure that any volatile components remain in the test sample during the Raman measurement cycle. One non-limiting example of a suitable Raman spectrometer comprising an automatic sampler is the PROCESS INSTRUMENTS® PI-200-AS AutoSampler.

In some embodiments, the laser in the Raman spectrometer may vary in wavelength over time or may be replaced with another laser that has a slightly different output wavelength. To compensate for any variations that occur in a laser's wavelength, in some embodiments, the described methods comprise automatically updating the laser's wavelength.

Figure 3:
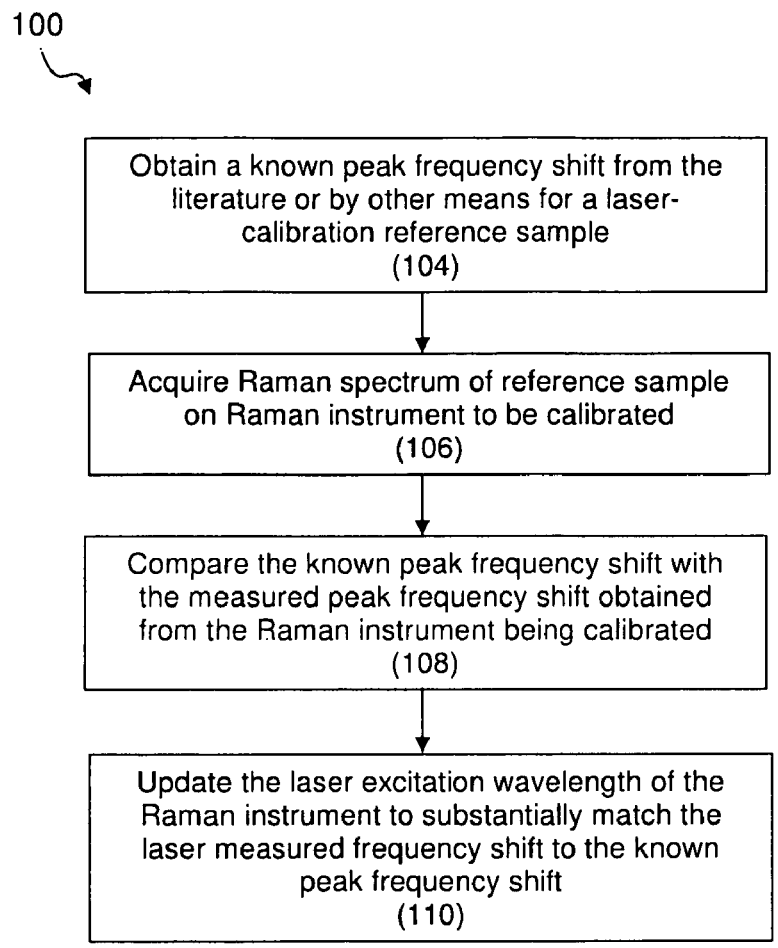
FIG. 3 illustrates a flow chart of a representative embodiment of a method for automatically updating a laser excitation wavelength in the Raman spectrometer.

While the laser may be automatically updated in any suitable manner, FIG. 3 shows a representative embodiment of a method for automatically updating the laser's wavelength. Specifically, FIG. 3 shows the method 100 may begin at step 104 by obtaining a known peak frequency shift for a laser-calibration reference sample. This step may include obtaining a known frequency shift from the literature or by other means. The laser-calibration reference sample may include any suitable pure reference sample, such as, but not limited to, a pure hydrocarbon, alcohol, high-pressure gas, or other material having a known peak frequency shift. However, because pure hydrocarbons may be easily flushed from the sample cell and have other beneficial characteristics, in some presently discussed embodiments, the laser-calibration reference sample used to calibrate the laser wavelength (or the first laser-calibration reference sample, for simplicity) comprises a pure hydrocarbon. As used herein, the term pure hydrocarbon may refer to any organic chemical consisting entirely of hydrogen and carbon that is suitable for use in a Raman spectrometer, and which is pure enough that only the hydrocarbon is detected when it is analyzed by a Raman spectrometer. Some examples of suitable pure hydrocarbons comprise m-xylene, o-xylene, p-xylene, benzene, and toluene. However, due to its relatively low toxicity and cost, in some presently preferred embodiments, toluene is used as the pure hydrocarbon.

FIG. 3 shows the method further comprises step 106 of acquiring a Raman spectrum of the reference sample on a Raman instrument to be calibrated. Both the known peak frequency shift of the laser-calibration reference sample (e.g., a pure hydrocarbon, such as toluene) and the associated laser excitation wavelength may be obtained in any suitable manner. For example, the known peak frequency shift of the chemical in the first laser-calibration reference sample (e.g., a pure hydrocarbon) and the associated laser excitation wavelength can be obtained from literature or through experimentation on one or more Raman spectrometers.

Once the known peak frequency shift and associated laser excitation wavelength of the laser-calibration reference sample (e.g., the pure hydrocarbon) are obtained, FIG. 3 shows the method 100 continues at step 108 by comparing the known peak frequency shift with the measured peak frequency shift obtained from the Raman instrument being calibrated. For instance, if the known peak frequency shift of the laser-calibration reference sample were for toluene, the laser-calibration reference sample would also be toluene. By determining the difference between the known peak frequency shift and the peak frequency shift of the laser-calibration reference sample and by using the laser excitation wavelength from the known peak frequency shift, the operator or computer interface may determine the actual laser excitation wavelength used to measure the second laser-calibration reference sample.

Next, at step 110, the method updates the laser excitation wavelength of the Raman instrument to substantially match the laser measured frequency shift to the know peak frequency shift. Accordingly, the described methods may be used to automatically recalibrate a laser's wavelength to adjust for slight variations in the laser's wavelength over time or when one laser replaces another laser.

The olefin concentration of one or more samples of an olefin-containing fuel is determined according to the present invention. In one non-limiting example, the method includes obtaining a linear calibration curve showing the ratio of the olefin area divided by the area of the chemical (e.g., toluene) in a pure reference sample (referred to as the linear-calibration reference sample) vs. the known olefin vol % concentrations for a plurality of simulated fuel samples. The linear-calibration reference sample may comprise any pure chemical that is suitable for use with a Raman spectrometer, is suitable for being mixed with an olefin containing fuel, and which produces a peak frequency shift for a single chemical. For example, the linear-calibration reference sample may comprise a pure hydrocarbon (e.g., toluene, m-xylene, o-xylene, p-xylene, benzene, etc.), an alcohol (e.g., methanol, ethanol, butanol, n-propanol, iso-propanol, etc.), a high pressure gas, or the like. Although not necessary, in some embodiments, the linear-calibration reference sample comprises the same chemical as the first and second laser-calibration reference sample.

Figure 4:
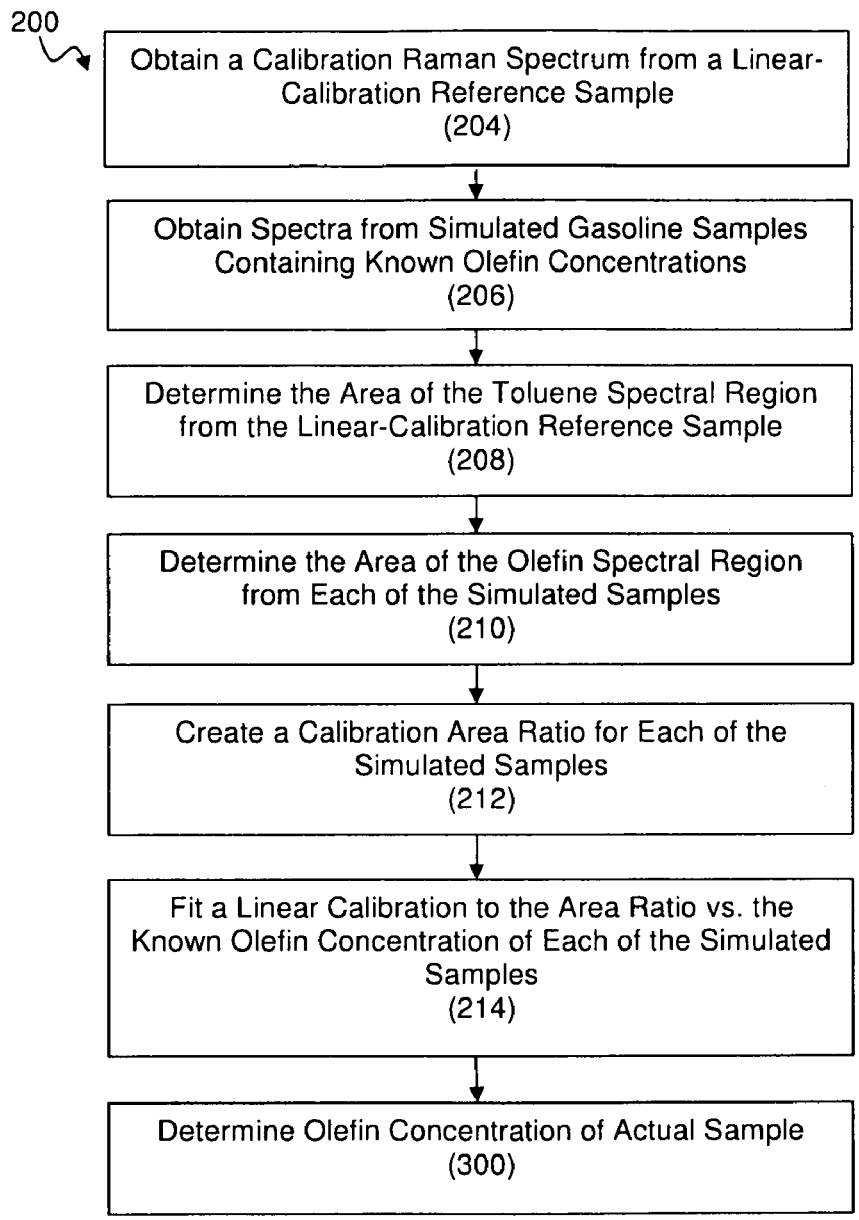
FIG. 4 illustrates a flow chart of a representative embodiment of a method for creating a linear calibration that is fit to a plot of the calibration area ratio vs. the known olefin concentration of a plurality simulated fuel samples.
Figure 5:
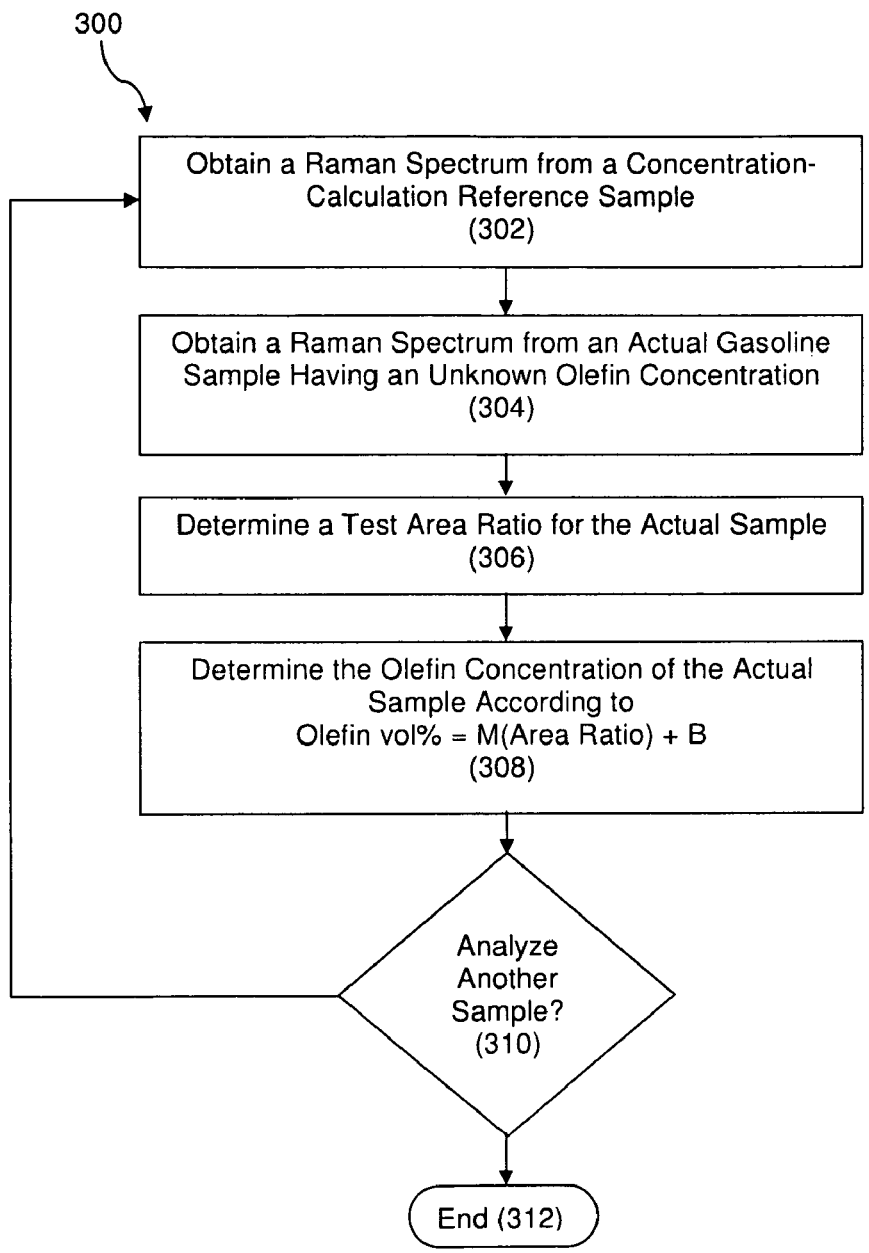
FIG. 5 illustrates a flow chart of a representative embodiment of a method for determining the olefin concentration of a olefin-containing fuel.

Using the linear olefin calibration curve, one may easily determine the vol % olefin in a fuel sample by dividing the area of the olefin spectral region by the area of the spectral region of the chemical in the linear-calibration reference sample (e.g., toluene) and then applying that value to the calibration curve. FIGS. 4 and 5 illustrate a non-limiting example of such a method. It should be noted, however, that this method may be modified in any suitable manner that allows it to fulfill its intended purpose. In one example, the various elements of the method may be rearranged in any suitable manner. In another example, while the method illustrated in FIGS. 4 and 5 focuses on determining the olefin concentration of gasoline samples, a similar method may be used to determine the olefin concentration of any other suitable olefin-containing fuel. In still another example, while the following method uses toluene as the chemical in the linear-calibration reference sample, the method may be performed with any other suitable pure reference sample, including any other suitable pure hydrocarbon, alcohol, etc.

FIG. 4 provides a flow chart of a representative embodiment of a method 200 for generating a linear calibration that can be used to determine the olefin concentration in actual fuel samples. Generally, FIG. 4 includes step 204 of obtaining a Raman spectrum (referred to as a calibration Raman spectrum) from a linear-calibration reference sample (e.g., a pure hydrocarbon, such as toluene). At step 206, the method obtains Raman spectra from a plurality of simulated gasoline samples containing known olefin concentrations. At this point, the Raman spectra may be collected from any number of simulated gasoline samples. For instance, Raman spectra may be collected from 2, 3, 4, 5, or more simulated gasoline samples. Similarly, the simulated gasoline samples may have any suitable olefin concentration. Generally, however, the simulated gasoline samples have known olefin concentrations that are near and/or surround the olefin concentrations that would be expected to be found in actual gasoline samples. For example, the simulated gasoline samples may comprise known olefin concentrations that are selected from about 0% to about 35%, from about 0% to about 25%, and from about 0% to about 15%, by volume. It will be appreciated that as more simulated gasoline samples are analyzed, a more accurate linear calibration curve may be generated.

Figure 6A:
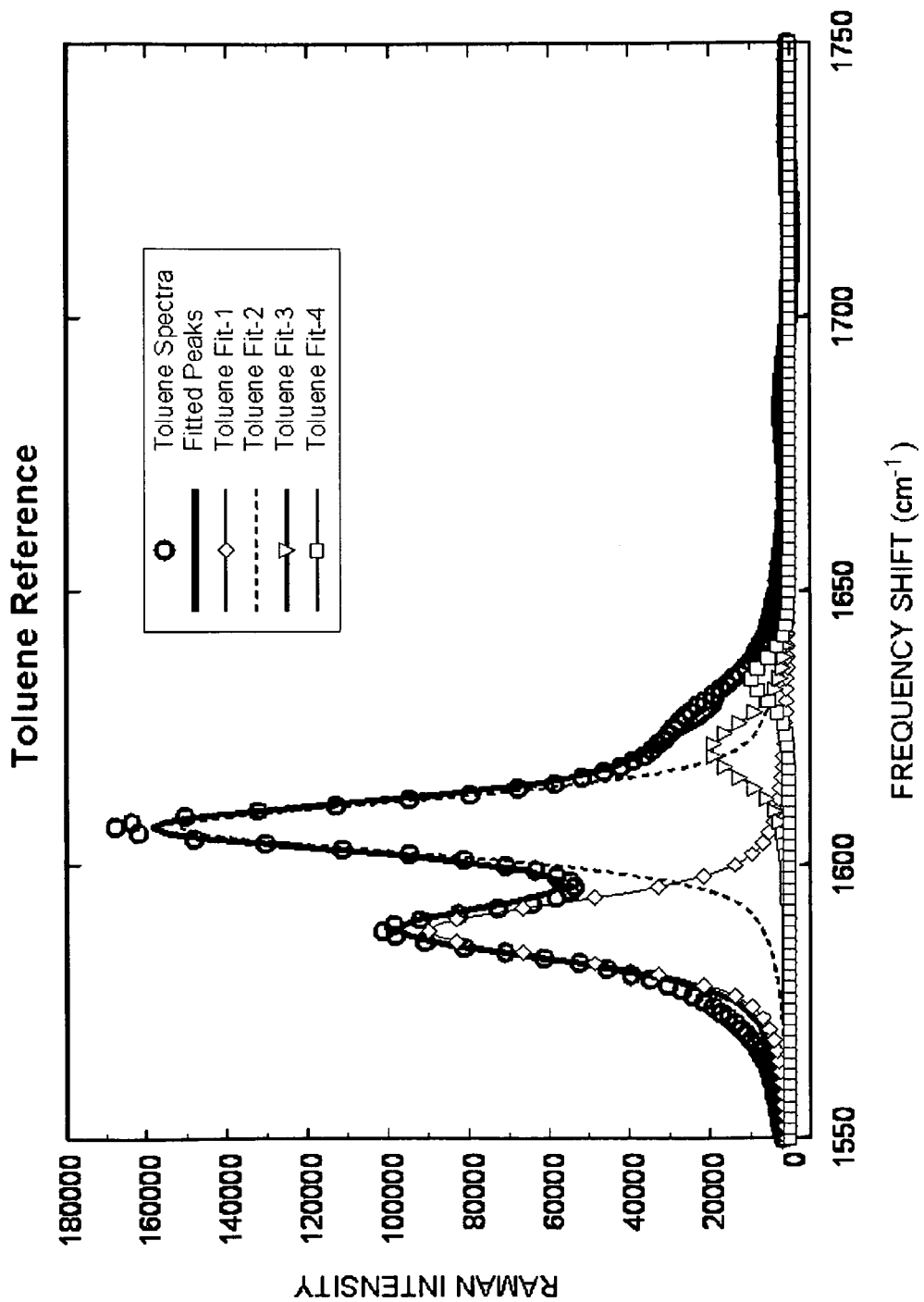
FIG. 6A illustrates a representative embodiment of a Raman spectrum from a toluene reference sample.
Figure 6B:
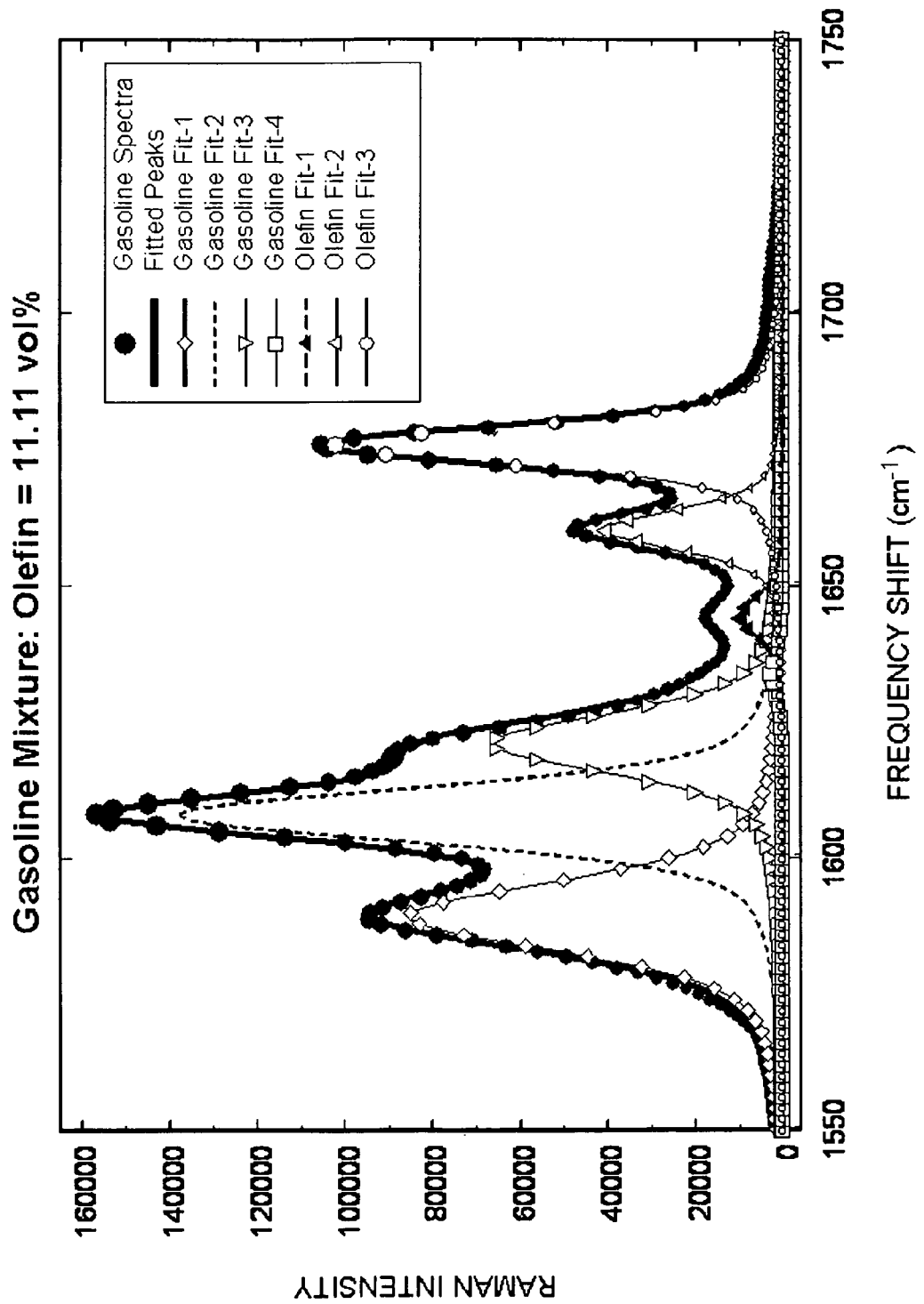
FIG. 6B illustrates a representative embodiment of a Raman spectrum from a gasoline sample comprising about 11.11% olefins, by volume.

At steps 208 and 210, the method continues by determining the area in the chemical (e.g., toluene) spectral region from the calibration Raman spectrum of the linear-calibration reference sample and the olefin spectral region (e.g., about 1635 to about 1725 cm$^{-1}$) from the Raman spectrum for each of the simulated gasoline samples. The area in the spectral region of the chemical (e.g., toluene) in the linear-calibration reference sample and the olefin spectral regions can be determined in any suitable manner. By way of illustration, FIGS. 6A and 6B show that each desired Raman peak can be fit with a Gaussian-Lorentzian function and that the area under the peaks can be calculated by the computer interface. Specifically, FIG. 6A shows toluene peaks from the calibration Raman spectrum of the linear-calibration reference sample and FIG. 6B illustrates the olefin and gasoline peaks from the Raman spectrum of a gasoline sample comprising 11.11% olefins, by volume. In FIGS. 6A and 6B, the spectral regions for the toluene and olefin, respectively, are indicated by the hollow circles.

In some embodiments, the portions of the area of the chemical spectral region of the linear-calibration reference sample and the olefin spectral regions that are measured to calculate the concentration of chemicals in the test sample may overlap each other. In one example, where the chemical in the linear-calibration reference sample is toluene, the toluene spectral region is measured from about 1540 to about 1660 cm$^{-1}$ and the olefin spectral regions from the simulated gasoline samples, or from a sample of another olefin-containing fuel, is measured from about 1625 to about 1730 cm$^{-1}$. In another presently preferred example, however, where the linear-calibration reference sample is toluene, the toluene spectral region is measured from about 1550 to about 1650 cm$^{-1}$ and the olefin spectral regions are measured from about 1635 to about 1725 cm$^{-1}$.

Returning to FIG. 4, step 212 creates a calibration area ratio for each of the simulated gasoline samples. This calibration area ratio may be made by dividing the area in the olefin spectral region (e.g., about 1635 to about 1725 cm$^{-1}$) in each simulated gasoline sample by the area of the spectral region (e.g., about 1550 to about 1650 cm$^{-1}$) of the chemical (e.g., toluene) from the linear-calibration reference sample. In other words, a calibration area ratio for each of the simulated gasoline samples is calculated by the formula (Area in the Olefin Spectral Region/Area in the Spectral Region of the Chemical (e.g., toluene) in the Linear-Calibration Reference Sample).

Figure 7:
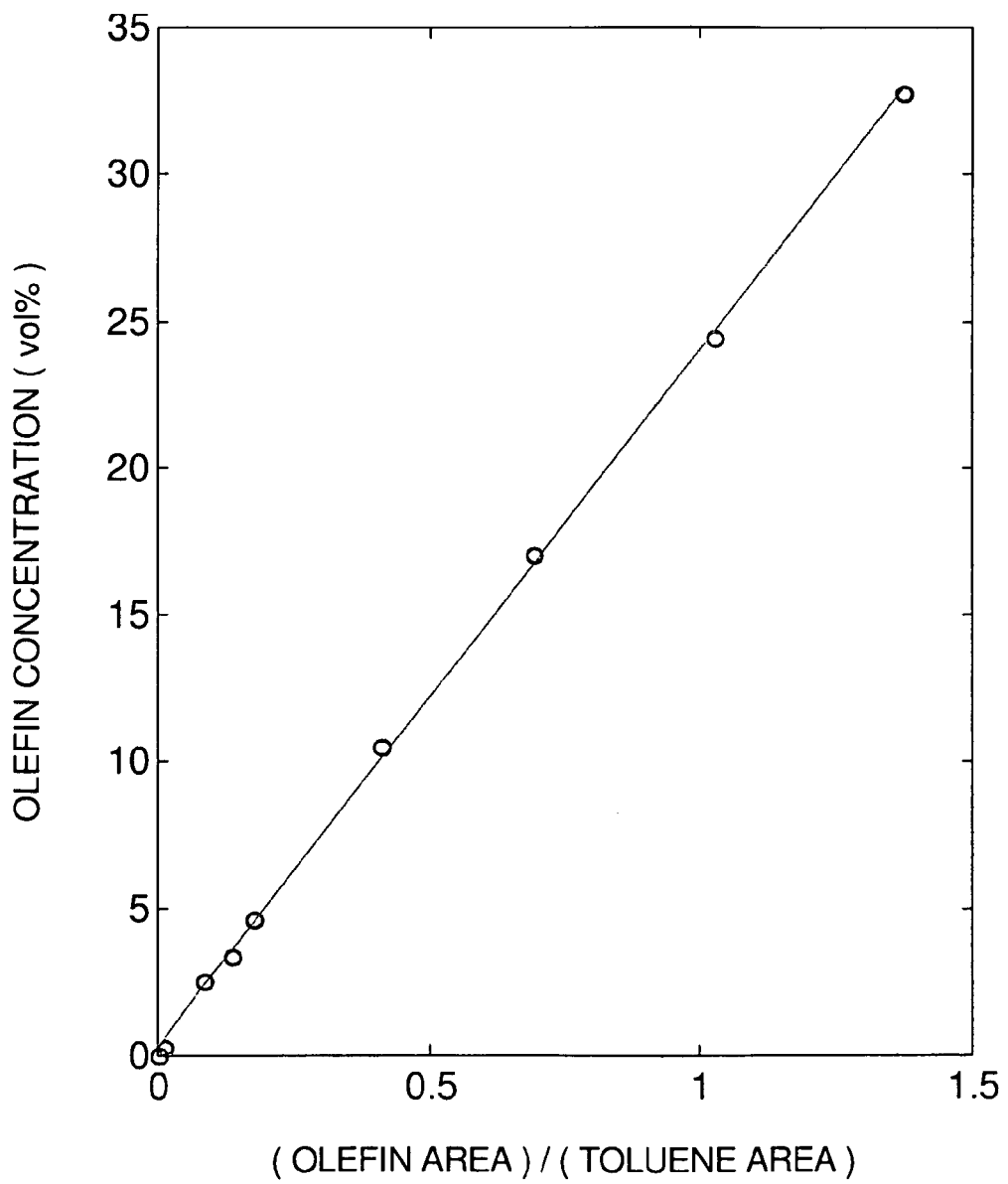
FIG. 7 illustrates a representative embodiment of a linear calibration curve of the calibration area ratio vs. the known olefin concentration of a plurality of simulated fuel samples.

At step 214 the method continues by creating the linear calibration curve. This linear calibration curve may be made in any suitable manner, including through the use of a least squares fit. In one example, FIG. 7 shows that the calibration area ratio and the known olefin concentration of several of the simulated gasoline samples are plotted onto a graph. While at least two simulated gasoline samples must be plotted to form a linear calibration curve, more data points will improve the accuracy of the linear calibration curve. The linear calibration of the plot may be described by the formula (Olefin vol %=M·(calibration area ratio)+B). In this formula, M describes the slope of the linear calibration curve, B describes the Y-intercept of the calibration curve, and Olefin vol % describes the olefin concentration in the test sample, by percent of the test sample's total volume. Additionally, in the example provided in FIG. 7, the calibration plot has a standard error of prediction for all of the simulated gasoline samples of about 0.26 volume percent.

Returning to FIG. 4, after obtaining a suitable calibration curve, the method may proceed with step 300 and determine the olefin concentration in a gasoline sample.

With a suitable linear calibration curve, the slope (M) and Y-intercept (B) may be determined, and the equation describing the linear calibration curve can be used directly with other Raman spectrometers to determine the olefin concentration of an olefin-containing fuel, such as gasoline. Accordingly, in some embodiments, after the initial calibration, subsequent users of the same or different Raman Spectrometer are not required to perform instrument calibration with a series of olefin dilutions. In other words, the linear calibration curve can be reused with the same spectrometer and/or be imported to another spectrometer.

FIG. 5 shows that the slope (M) and Y-intercept (B) of the linear calibration curve determined in FIG. 4 can be used to determine the concentration of a sample of gasoline ("actual sample") that has an unknown olefin concentration. Specifically, step 302 includes obtaining a Raman spectrum from a pure reference sample, referred to, for simplicity, as a concentration-calculation reference sample. This concentration-calculation reference sample may comprise any pure chemical that is suitable for use with a Raman spectrometer, is suitable for being mixed with an olefin containing fuel, and which produces a peak frequency shift for a single chemical. However, because hydrocarbons are often a component in many olefin-containing fuel blends, a pure hydrocarbon, such as toluene, is used as the concentration-calculation reference sample. Additionally, in some embodiments, the concentration-calculation reference sample comprises the same chemical composition as the first laser-calibration reference sample, the second laser-calibration reference sample, and/or the linear-calibration reference sample.

The Raman spectrum for the concentration-calculation reference sample may be obtained in any suitable manner. By way of example, the Raman spectrum in step 302 may comprise the Raman spectrum from the second laser-calibration reference sample discussed in box 108 of FIG. 3 or the Raman spectrum from the linear-calibration reference sample in box 204 of FIG. 4.

At step 304 the method continues by obtaining a Raman spectrum for the actual sample. Next, step 306 determines a test area ratio for the actual sample. While this test area ratio can be created in any suitable manner, in the disclosed embodiments, the test area ratio is made by dividing the area of the olefin spectral region in the actual sample by the area of the chemical (e.g., toluene) spectral region in the concentration-calculation reference sample.

At step 308 the test area ratio may be substituted for the calibration area ratio in the equation describing the linear calibration curve (e.g., Olefin vol %=M·(area ratio)+B). Then, using the slope (M) and Y-intercept (B) of the linear calibration curve, the olefin concentration, in volume percent, of the actual sample may be obtained in any suitable manner (e.g., algebraically).

After determining the olefin concentration of an actual sample, the method may either end at 312 or be repeated by returning to step 302 to determine the olefin concentration in another actual sample.

In addition to the aforementioned benefits and advantages, the described methods for determining the olefin concentration of an olefin-containing fuel, such as gasoline, provide several additional beneficial features. In one example, the described methods account for instrument throughput differences caused by variances in fiber-optic coupling, laser power, filter efficiency, dirty sample cell window, optical lens clouding, and the like. The described methods account for these throughput differences by the creation of the area ratio (e.g., the test and/or the calibration area ratio) of the area in the olefin spectral region to the area in the adjacent chemical (e.g., toluene) spectral region of the chemical in the concentration-calculation reference sample. Indeed, because the area of each spectral region (e.g., the olefin and toluene regions) is determined, in part, by the instrument's throughput, dividing the area of the spectral regions automatically corrects for differences in the instrument's throughput. For instance, fluctuations in the area of the olefin spectral regions caused by changes in the laser's intensity or a buildup on the flow cell window can be removed by dividing the area of the olefin spectral region of the actual sample by the area of the toluene spectral region from the concentration-calculation reference sample. By way of illustration, if the laser power were to decrease by 10%, the area of both the olefin spectral region and the chemical (e.g., toluene) spectral region of the chemical in the concentration-calculation reference sample would decrease by the same amount. Thus, by dividing the area of the olefin spectral region by the area of the chemical spectral region in the concentration-calculation reference sample, the described methods automatically compensate for throughput variances.

In another example that was previously mentioned, the linear calibration may be used on more than one Raman spectrometer. This ability to use the slope/Y-intercept from an initial linear calibration on one Raman spectrometer with another spectrometer may be made possible by the close and/or overlapping spectral proximity between the spectral regions of the olefin and the chemical (e.g., toluene) in the concentration-calculation reference sample. Indeed, it is theorized that if the olefin spectral region and the chemical spectral region of the chemical in the concentration-calculation reference sample were spaced further apart, then the area ratio between the two would be influenced by variations in the quantum efficiency curves from different CCD cameras. Accordingly, the slope/intercept from the initial calibration could not be used on all Raman spectrometers. In contrast, it is believed that having the measured olefin spectral region overlap with the measured chemical spectral region of the concentration-calculation reference sample removes the quantum efficiency variance and allows the slope and Y-intercept from the initial linear calibration to be used on a variety of Raman spectrometers.

In yet another example, the described methods may be used to accurately determine the olefin concentration of a variety of olefin-containing fuels. For instance, because the linear calibration only utilizes the area from the olefin spectral region (e.g., 1635 to 1725 $cm^{-1}$), the linear calibration may eliminate problems that can arise from spectral variations between different gasoline mixtures.

Figure 8:
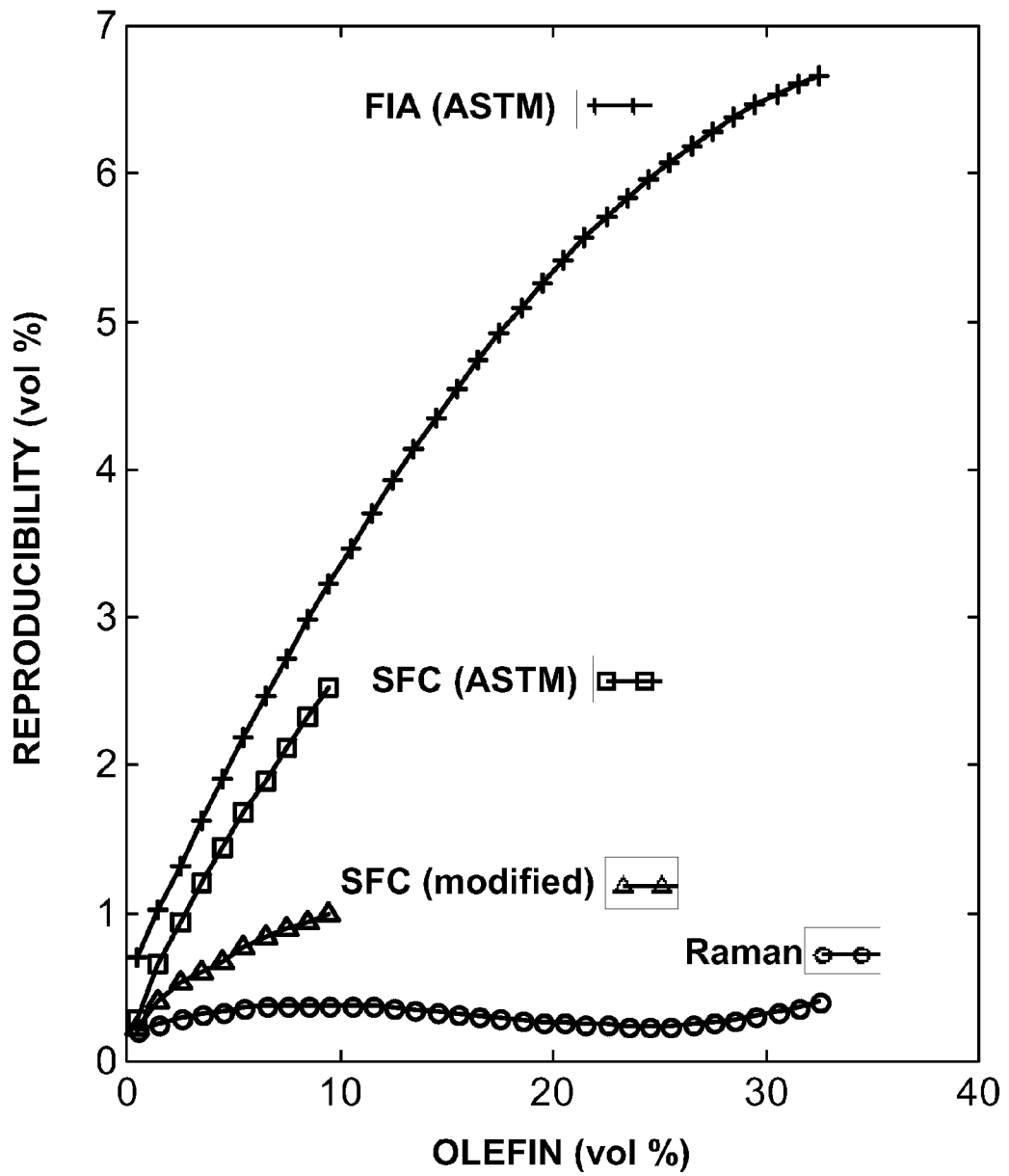
FIG. 8 illustrates a representative embodiment of experimental results comparing the described methods with some conventional methods for determining olefin concentrations in olefin-containing fuels.

It will be appreciated that the described methods allow Raman spectrometers to accurately and repeatably determine olefin concentrations in an olefin-containing fuel. Indeed, the accuracy and disclosed method is far superior to other commonly used methods to determine olefin concentration. FIG. 8 illustrates experimental results comparing the reproducibility of four different test methods as a function of olefin concentrations.

More specifically, FIG. 8 illustrates the reproducibility between two different instruments for each of four different methods for determining olefin concentrations in an olefin-containing fuel. As shown in FIG. 8, the four methods comprise the described method ("Raman"), the SFC modified test method ("SFC (modified)"), the SFC test method ASTM-D6550-05 ("SFC (ASTM)"), and the fluorescent indicator adsorption test method ("FIA (ASTM)"). In FIG. 8, the reproducibility variable is defined as a quantitative measure of the methods' precision. The reproducibility variable represents the maximum expected difference between two instruments implementing the same method and analyzing identical samples. Additionally, in FIG. 8, the line labeled Raman represents the reproducibility of two Raman spectrometers that use identical slopes (M) and Y-intercepts (B) to determine the olefin concentration, in volume percent, of identical samples having increasing olefin concentrations.

FIG. 8 illustrates that, unlike other methods (e.g., the SFC (modified), SFC (ASTM), and FIA (ASTM) methods), the reproducibility of the described methods does not substantially degrade at higher olefin concentrations. In fact, FIG. 8 shows that at olefin concentrations at or below about 35%, the precision in reproducibility of the described methods remains below about 0.5%. In contrast, FIG. 8 illustrates that the reproducibility of the conventional testing methods (e.g., the SFC (modified), the SFC (ASTM), and the FIA (ASTM test methods) rapidly decreases as olefin concentrations increase. As a result, gasoline producers using the described methods may more accurately determine olefin levels in gasoline mixtures compared to the SFC modified, the SFC (ASTM), the FIA (ASTM), and/or other similar methods.

The described embodiments and examples are all to be considered in every respect as illustrative only, and not as being restrictive. The scope of the invention is, therefore, indicated by the appended claims, rather than by the foregoing description. All changes that come within the meaning and range of equivalency of the claims are to be embraced within their scope.

The invention claimed is:

1. A method for determining an olefin concentration of an olefin-containing fuel, the method comprising:

obtaining a linear calibration curve described by an equation:

Olefin vol %=$M$·(area ratio)+$B$ wherein:
Olefin vol % comprises an actual olefin concentration, by volume percent;
M comprises a slope of the linear calibration curve;
"area ratio" comprises a ratio of a first area in an olefin spectral region compared to a second area in a first chemical spectral region of a Raman spectrum of a first chemical in a linear-calibration reference sample; and
B comprises a Y-intercept of the linear calibration curve;

obtaining a first Raman spectrum from a concentration-calculation reference sample;

obtaining a second Raman spectrum from an olefin-containing fuel sample having an unknown olefin concentration;

calculating a test area ratio by dividing the first area in the olefin spectral region of the second Raman spectrum by the second area in a second chemical spectral region of a second chemical in the first Raman spectrum obtained from the concentration-calculation reference sample; and calculating the unknown olefin concentration according to the linear calibration curve.

2. The method of claim 1, wherein the first chemical and the second chemical comprise the same pure substance.

3. The method of claim 1, wherein the first chemical and the second chemical are selected from an alcohol, m-xylene, o-xylene, p-xylene, benzene, and toluene.

4. The method of claim 1, wherein the second chemical comprises toluene.

5. The method of claim 1, wherein the second chemical spectral region is between about 1550 and about 1650 $cm^{-1}$, and wherein the olefin spectral region is between about 1635 and about 1725 $cm^{-1}$.

6. The method of claim 1, wherein the olefin-containing fuel sample comprises a gasoline mixture.

7. The method of claim 1, wherein the first Raman spectrum and the second Raman spectrum are obtained using a Raman spectrometer, wherein the Raman spectrometer comprises a near-infrared Raman spectrometer.

8. The method of claim 1, wherein the linear calibration curve is obtained by the method comprising:

obtaining a first calibration Raman spectrum from the linear-calibration reference sample;

obtaining a second calibration Raman spectra from each of a plurality of simulated olefin-containing fuel samples comprising known olefin concentrations;

creating a calibration area ratio for each of the simulated samples by individually dividing the area of the olefin spectral region from each of the simulated samples by the area of the first chemical spectral region from the linear-calibration reference sample; and fitting the linear calibration curve to a plot of the calibration area ratio verses the known olefin concentration of at least two of the simulated olefin-containing fuel samples.

9. The method of claim 8, wherein the simulated olefin-containing fuel samples include olefin concentrations ranging from at least 0 to 35 vol %.

10. The method of claim 8, wherein the simulated olefin-containing fuel samples include olefin concentrations ranging from at least 0 to 15 vol %.

11. The method of claim 8, wherein the olefin spectral region from each of the simulated samples overlaps the first chemical spectral region of the linear-calibration reference sample.

12. The method of claim 8, wherein the first chemical spectral region is between about 1540 and about 1660 $cm^{-1}$.

13. The method of claim 8, wherein the olefin spectral region is between about 1635 and about 1725 $cm^{-1}$.

14. The method of claim 1, wherein the first Raman spectrum and the second Raman spectrum are obtained using a Raman spectrometer having a laser to provide optical excitation at a given wavelength.

15. The method of claim 14, further comprising the step of automatically compensating for variations in the laser wavelength in the Raman spectrometer.

16. The method of claim 15, wherein the step of automatically compensating for variations in the laser wavelength comprises:

determining a laser excitation wavelength, which was used to obtain a known Raman spectrum from a laser-calibration reference sample;

comparing the known Raman spectrum with a reference Raman spectrum of the laser-calibration reference sample obtained using the Raman spectrometer;

determining an actual laser excitation wavelength used to obtain the reference Raman spectrum from the laser-calibration reference sample; and changing the actual laser excitation wavelength to substantially match the laser excitation wavelength that was used to obtain the known Raman spectrum.

17. The method of claim 1, wherein the olefin-containing fuel sample comprises a gasoline mixture, wherein the concentration-calculation reference sample is toluene, wherein the second chemical spectral region is between about 1550 and about 1650 $cm^{-1}$, and wherein the olefin spectral region is between about 1635 and about 1725 $cm^{-1}$.

18. The method of claim 17, wherein the Raman spectrum is obtained using a Raman spectrometer having a laser to provide optical excitation at a given wavelength.

19. The method of claim 18, wherein the Raman spectrometer comprises a near-infrared Raman spectrometer.

20. The method of claim 19, further comprising the step of automatically compensating for variations in the laser wavelength in the Raman spectrometer throughput.

* * * * *